(12) United States Patent
Pedersen et al.

(10) Patent No.: US 6,656,107 B1
(45) Date of Patent: Dec. 2, 2003

(54) BRACHYTHERAPY SEED APPLICATORS

(75) Inventors: Laust Pedersen, Santa Barbara, CA (US); Jerry R. Barber, Ventura, CA (US)

(73) Assignee: Mentor Corporation, Santa Barbara, CA (US)

( * ) Notice: Subject to any disclaimer, the term of this patent is extended or adjusted under 35 U.S.C. 154(b) by 0 days.

(21) Appl. No.: 10/155,905

(22) Filed: May 24, 2002

(51) Int. Cl.[7] .......................... A61M 36/00; A61M 5/00
(52) U.S. Cl. ................................ 600/7; 600/3
(58) Field of Search ........................ 600/7; 604/61, 604/62, 63, 64; 206/535; 221/198, 232, 279, 18

(56) References Cited

U.S. PATENT DOCUMENTS

| | | | | |
|---|---|---|---|---|
| 2,620,796 A | * | 12/1952 | Eriksen et al. | 604/62 |
| 4,451,254 A | * | 5/1984 | Dinius et al. | 604/62 |
| 5,522,797 A | * | 6/1996 | Grimm | 604/61 |
| 6,213,932 B1 | * | 4/2001 | Schmidt | 600/7 |
| 6,267,718 B1 | * | 7/2001 | Vitali et al. | 600/7 |
| 6,270,472 B1 | * | 8/2001 | Antaki et al. | 604/61 |
| 6,358,195 B1 | * | 3/2002 | Green et al. | 600/7 |
| 6,454,696 B1 | * | 9/2002 | Kindlein et al. | 600/7 |

* cited by examiner

*Primary Examiner*—Eric F. Winakur
*Assistant Examiner*—Nikita Veniaminov
(74) *Attorney, Agent, or Firm*—Fish & Richardson P.C., P.A.

(57) ABSTRACT

The invention features brachytherapy applicators for delivering radioactive seeds to a patient. Specifically, the invention provides brachytherapy applicators in which a seed magazine is removably held within a chuck by a magazine retaining structure. The magazine retaining structures described herein are designed such that a seed magazine can be readily inserted into or removed from a brachytherapy applicator. In addition, magazine retaining structures are designed such that they will not become jammed, even when blood cells or other particles enter the applicator during a brachytherapy procedure and become lodged near the seed magazine and the magazine retaining structure.

21 Claims, 21 Drawing Sheets

BRACHYTHERAPY SEED APPLICATORS

TECHNICAL FIELD

This invention relates to devices for delivering brachytherapy seeds to an individual.

BACKGROUND

Brachytherapy is a form of cancer treatment in which radiation sources are placed inside a patient's body to irradiate a tumor. In brachytherapy, a surgeon usually implants several radioactive seeds in or around a tumor, thus providing a radiation dose to the tumor. Careful placement of the radioactive seeds allows localized and precise irradiation of the tumor. Because the radiation dose diminishes rapidly outside the radioactive seed, the radiation dose to surrounding healthy tissues is minimized. Many forms of cancer respond to brachytherapy, including several forms of prostate cancer. Brachytherapy generally is less invasive than surgery, usually results in fewer side effects than surgery or external beam radiation, allows for a short recovery time, and reduces the impact on the patient's quality of life.

SUMMARY

The invention features brachytherapy applicators for delivering radioactive seeds to a patient. Specifically, the invention provides brachytherapy applicators in which a seed magazine is removably held within a chuck by a magazine retaining structure. The magazine retaining structures described herein are designed such that a seed magazine can be readily inserted into or removed from a brachytherapy applicator.

During brachytherapy procedures, blood cells can migrate from the patient into the applicator. These blood cells and other contaminants can become lodged in the applicator at or near the magazine retaining structure. The magazine retaining structures provided by the invention are designed such that they will not become jammed when blood cells or other particles enter the applicator during a brachytherapy procedure and remain in the applicator during cleaning and autoclaving. Clinicians performing brachytherapy procedures therefore can quickly and easily insert and remove empty magazines from the applicators provided herein, and can be assured that newly inserted seed magazines will be firmly held in place.

The invention features a brachytherapy applicator containing a needle and a chuck. The chuck can contain a slot for receiving a magazine containing radioactive seeds, and the chuck can be positioned such that seeds are delivered from the magazine to the needle. The chuck can contain a magazine retaining structure selected from the group consisting of a solid component and a component that contains at least two openings.

The magazine retaining structure can include a leaf spring having at least one protrusion (e.g., a ball like feature). The chuck can define a vent positioned behind the leaf spring. The magazine retaining structure can include a wire having a bulge. The chuck can define a groove, and the wire can be in the groove. The chuck can define a vent positioned behind the bulge. The magazine retaining structure can include a Bellville spring having a protrusion (e.g., a central dome). The chuck can define a vent positioned behind the Bellville spring.

The magazine retaining structure can be a component that contains at least two openings. The magazine retaining structure can include a hollow shell having a first end, wherein the first end defines an opening, and wherein the shell defines a vent, the opening and the vent being the at least two openings. The magazine retaining structure also can include a ball, wherein the shell retains the ball such that the ball is movably positioned at least partially within the shell, and a spring, wherein the shell retains the spring such that the spring exerts force against the ball such that the ball is pushed toward the first end to a position where the ball partially protrudes through the opening. The shell can define a second end, and the vent can be positioned at the second end. The shell can define a side region, and the vent can be positioned in the side region. The vent can be accessible through the chuck. At least a portion of an outer surface of the shell can contain a thread. The chuck can define first and second side portions, and at least one of the side portions can define an opening capable of receiving the magazine retaining structure. The magazine retaining structure can be removable from the applicator. The magazine retaining structure can be plastic, bronze, or stainless steel.

In another aspect, the invention features a brachytherapy applicator containing a needle and a chuck. The chuck can define a slot for receiving a magazine containing radioactive seeds, wherein the chuck is positioned such that the seeds are delivered from the magazine to the needle. The chuck also can contain a magazine retaining structure, wherein the magazine retaining structure includes a hollow shell defining a first end and a second end, wherein the first end defines an opening; a ball, wherein the ball is movably positioned at least partially within the hollow shell; and a spring, wherein the spring exerts force against the ball in a direction toward the first end such that the ball partially protrudes through the opening, and wherein at least one open space exists when the ball is fully engaged within the opening. The hollow shell can define a vent (e.g., a vent at the second end or a vent in a side region).

The invention also features a ball-plunger device containing a hollow shell, a ball, and a spring. The hollow shell can define a first end and an outer surface, wherein the first end defines an opening, and wherein the outer surface defines at least one thread and at least one vent. The ball can be movably positioned at least partially within the hollow shell. The spring can exert force against the ball in a direction toward the first end such that the ball partially protrudes through the opening. The hollow shell can define a second end, and the vent can be positioned at the second end. The hollow shell can define a side region, and the vent can be positioned in the side region. The hollow shell can define a second end, wherein the second end defines a head, and wherein the head contains a recess adapted to receive the mating end of an installation tool (e.g., a Phillips screwdriver). The head can contain a vent.

In another aspect, the invention features a hollow screw containing a shell structure, a ball and a spring. The shell structure can defines a first end and an outer surface, the first end can define an opening, the outer surface can define a vent, and at least a portion of the outer surface can contain a thread. The ball can be movably positioned at least partially within the shell structure. The spring can be positioned within the shell structure such that the spring exerts force against the ball in a direction toward the opening. The shell structure can define a second end, wherein the second end defines a head. The head can define the vent. The ball can protrude from the shell structure to a distance between about 0.01 inch and 0.1 inch.

In yet another aspect, the invention features a hollow screw containing a plastic shell structure, a ball, and a spring. The plastic shell structure can define a first end and an outer surface, wherein the first end defines an opening, and wherein at least a portion of the outer surface defines a thread. The ball can be movably positioned at least partially within the shell structure. The spring can be positioned within the shell structure such that the spring exerts force against the ball in a direction toward the opening. The shell structure can defines a second end, wherein the second end defines a head, and wherein the head defines a vent. The head can define a recess adapted to receive the mating end of an installation tool (e.g., a Phillips screwdriver).

The invention also features a hollow plastic screw containing a shell structure, a ball, and a spring. The shell structure can define a first end, a head, and an outer surface, wherein the first end defines an opening, and wherein at least a portion of the outer surface defines a thread. The ball can be movably positioned at least partially within the shell structure. The spring can be positioned within the shell structure such that the spring exerts force against the ball in a direction toward the opening. The head can define a recess adapted to receive the mating end of an installation tool (e.g., a Phillips screwdriver).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
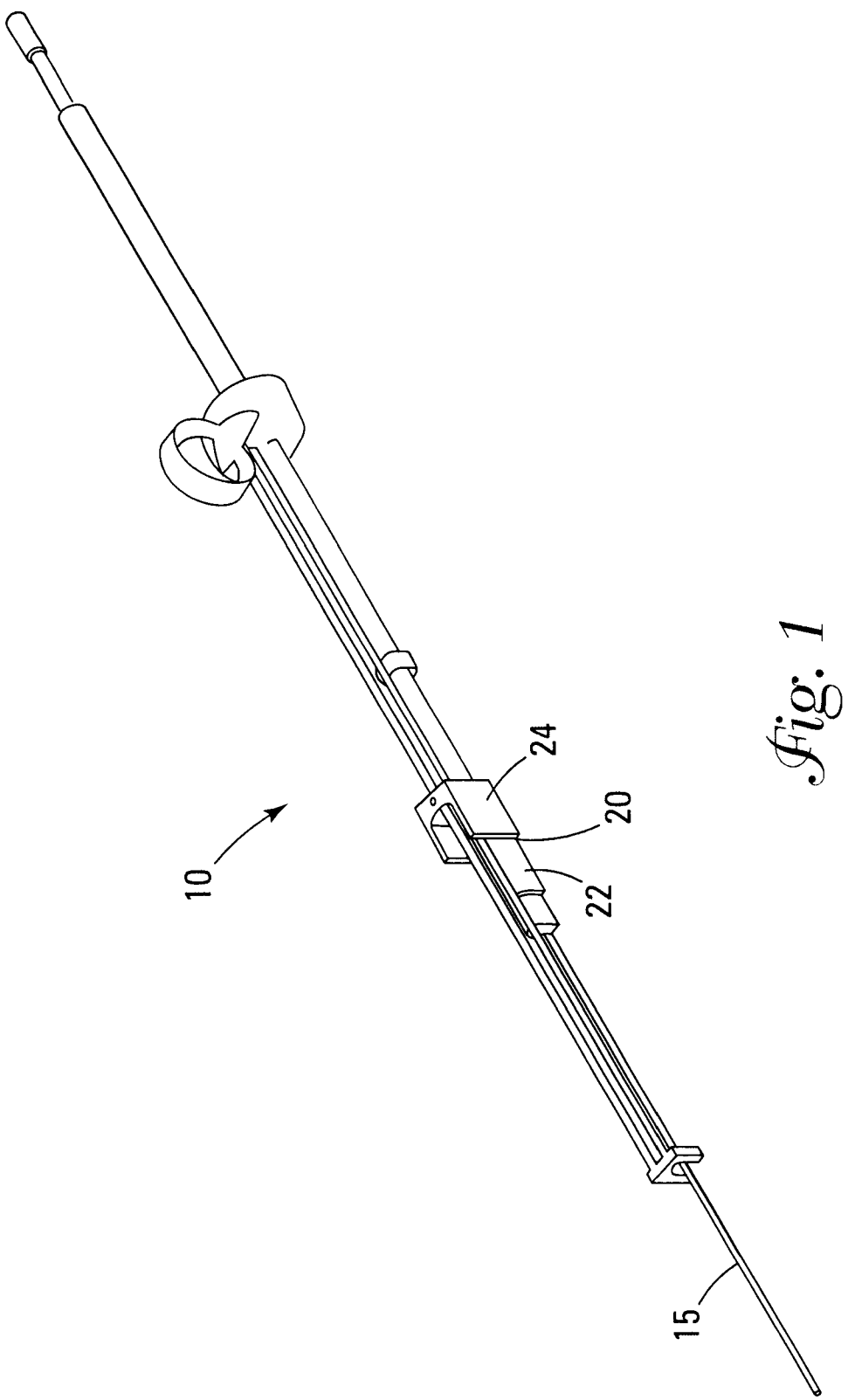
FIG. 1 is a side view of a brachytherapy applicator.

Brachytherapy applicators typically include a hollow needle that is insertable into a patient's body, a chuck for releasably holding the needle, and a seed magazine for holding and dispensing seeds into the chuck and the needle. The chuck typically contains a slot for insertion of the seed magazine. Brachytherapy applicators also can include, for example, a barrel connected to the chuck, a stylet that is extendable through the barrel, chuck, and hollow needle, and a base frame along which the needle, chuck, seed magazine, and barrel are slidably mounted.

The components of a brachytherapy applicator can be made from any suitable material. Any rigid metal or plastic material is particularly useful. For example, components of a brachytherapy applicator can be made from stainless steel, polyfluorocarbon, and/or any other suitable material. The brachytherapy applicators provided herein can contain components such as those disclosed in, for example, U.S. Pat. Nos. 5,860,909; 5,242,373; 4,700,692; 4,461,280; and 4,402,308.

Seed magazines typically are designed to contain radio-labeled seeds that are stacked parallel to each other. A spring-loaded magazine plunger can be biased against the seeds at the upper end of a magazine to facilitate seed movement into the chuck and to provide an indication to the operator that a seed has been dispensed from the magazine.

A seed magazine can be keyed to the chuck to prevent its incorrect insertion into the chuck. For example, a chuck can include an orientation pin extending into a slot in which the magazine is retained. The magazine can include a notch to mate with the orientation pin when the magazine is correctly oriented in the slot.

In the operation of a brachytherapy applicator for prostate gland treatment, the needle typically is first inserted into the patient's prostate gland in areas where seeds are to be implanted. The chuck of the applicator then can be coupled with the protruding end of the needle to prepare the applicator for use. The stylet, which is initially fully extended in the needle, can be retracted from the needle and the chuck, enabling a seed from the magazine to be positioned in the chuck for movement into the needle. As a seed moves into the chuck when the stylet is retracted, the extended magazine plunger can move further into the magazine, which will indicate to the operator that a seed has been positioned for transfer into the needle. The stylet then can be pushed through the barrel against the seed, forcing the seed through the needle and into the patient's body.

After a first seed has been implanted, the needle can be withdrawn from the patient's body by a particular distance, so that the next seed implanted is spaced apart from the first seed. The stylet can again be retracted to enable the next seed from the magazine to be positioned for movement into the needle. The stylet then can be advanced through the needle to force the next seed into the patient's body away from the first seed. This procedure can be repeated for subsequent seed implants. The operator can vary seed spacing as desired. In some embodiments, brachytherapy applicators include mechanisms for spacing seeds at reproducible increments as selected by the operator. See, e.g., U.S. Pat. No. 5,860,909.

The brachytherapy applicators provided herein contain structures for reversibly retaining a seed magazine, such that seed magazines can be readily inserted into or removed from the applicators. While a seed magazine is in an applicator, it is held in place by the magazine retaining structure. Magazine retaining structures typically are designed to hold a magazine in place during use, but permit the magazine to be readily removed by a clinician operating the applicator. When a seed magazine is empty, for example, it can be removed from the applicator, and a magazine that contains seeds can be inserted and held by the magazine retaining structure. The magazine retaining structures described herein are designed such that they will not become jammed when, for example, blood cells or other particles enter the applicator during a brachytherapy procedure and are retained within the applicator during cleaning, autoclaving, and repeated use.

The magazine retaining structures provided herein can be solid structures (e.g., springs or wires), or can be components (e.g., ball-plungers) that have at least two openings. Magazine retaining structures also can be ball-plungers containing an opening (e.g., a circular opening with one or more notches), such that when the ball is fully engaged in the opening, at least one open space exists in the magazine retaining structure. A ball is fully engaged in the opening when it is pushed against the smallest inner diameter of the opening and cannot be further pushed through the opening. In addition, magazine retaining structures can be made from any suitable material. Materials that are particularly useful include those that are not adversely affected by autoclaving. Such materials can include plastic, stainless steel, and bronze. Other materials also can be used, regardless of their stability during autoclaving.

A magazine retaining structure can be permanently or removably installed within a brachytherapy applicator. Magazine retaining structures that are removable can be cleaned and then replaced in the brachytherapy applicator, or can be discarded and replaced with a different magazine retaining structure.

With reference to FIG. 1, the invention provides brachytherapy applicator 10 having needle 15 and chuck 20. Chuck 20 can be designed to receive a seed magazine that contains radiolabeled brachytherapy seeds. Chuck 20 also can be positioned such that the brachytherapy seeds are delivered from the seed magazine into needle 15. Chuck 20 can be a single unit (i.e., a one-piece chuck) or can be made up of more than one chuck (e.g., a cylindrical chuck 22 and a rectangular chuck 24).

Figure 2:
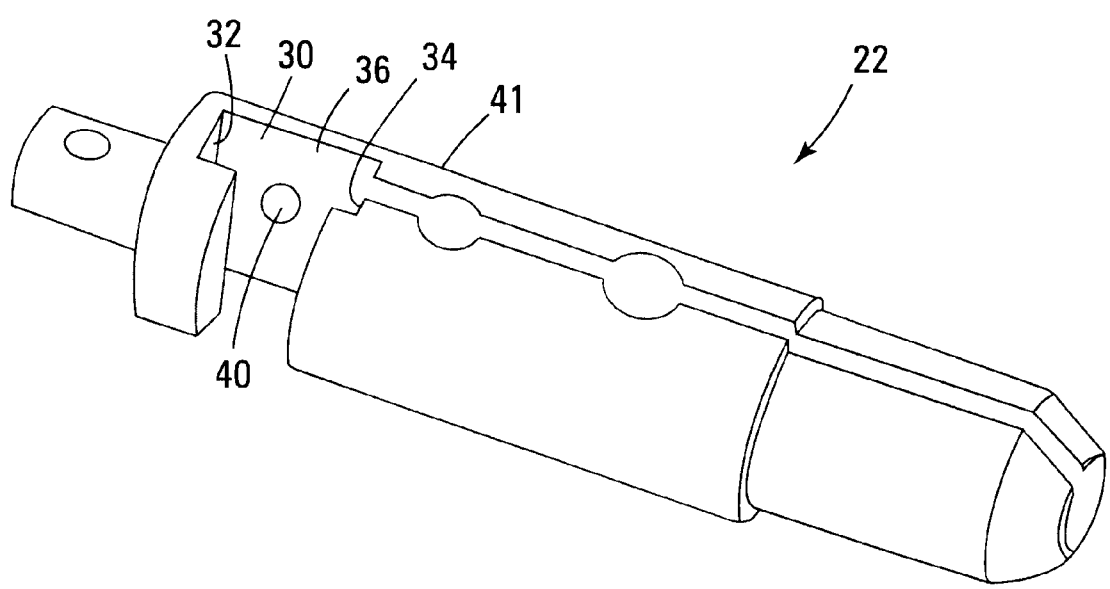
FIG. 2 is a side view of a chuck.

FIG. 2 is a side view of chuck 22, which contains slot 30 for a seed magazine. Slot 30 can have side surface 32, second side surface 34, and back surface 36. Slot 30 typically contains a mechanism for reversibly retaining a seed magazine such that the magazine is held in place during use but can be readily replaced with another seed magazine if desired by a clinician (e.g., a clinician conducting a brachytherapy procedure). A magazine retaining structure can be designed to interact releasably with a seed magazine, and can be positioned at any suitable location in or near slot 30. Magazine retaining structure 40, for example, can be positioned to protrude from back surface 36 of slot 30. In addition, magazine retaining structure 40 can be, for example, a solid structure (e.g., a spring or a wire) or a ball-plunger that has at least two openings. Such structures are described herein. Magazine retaining structures can be inserted into chuck 22 such that they extend into or through chuck 22, from back surface 36 toward the outer surface of the chuck (e.g., outer surface 41). Alternatively, a magazine retaining structure can be installed (e.g., removably or permanently) directly in slot 30 (e.g., on back surface 36 of slot 30).

Figure 3:
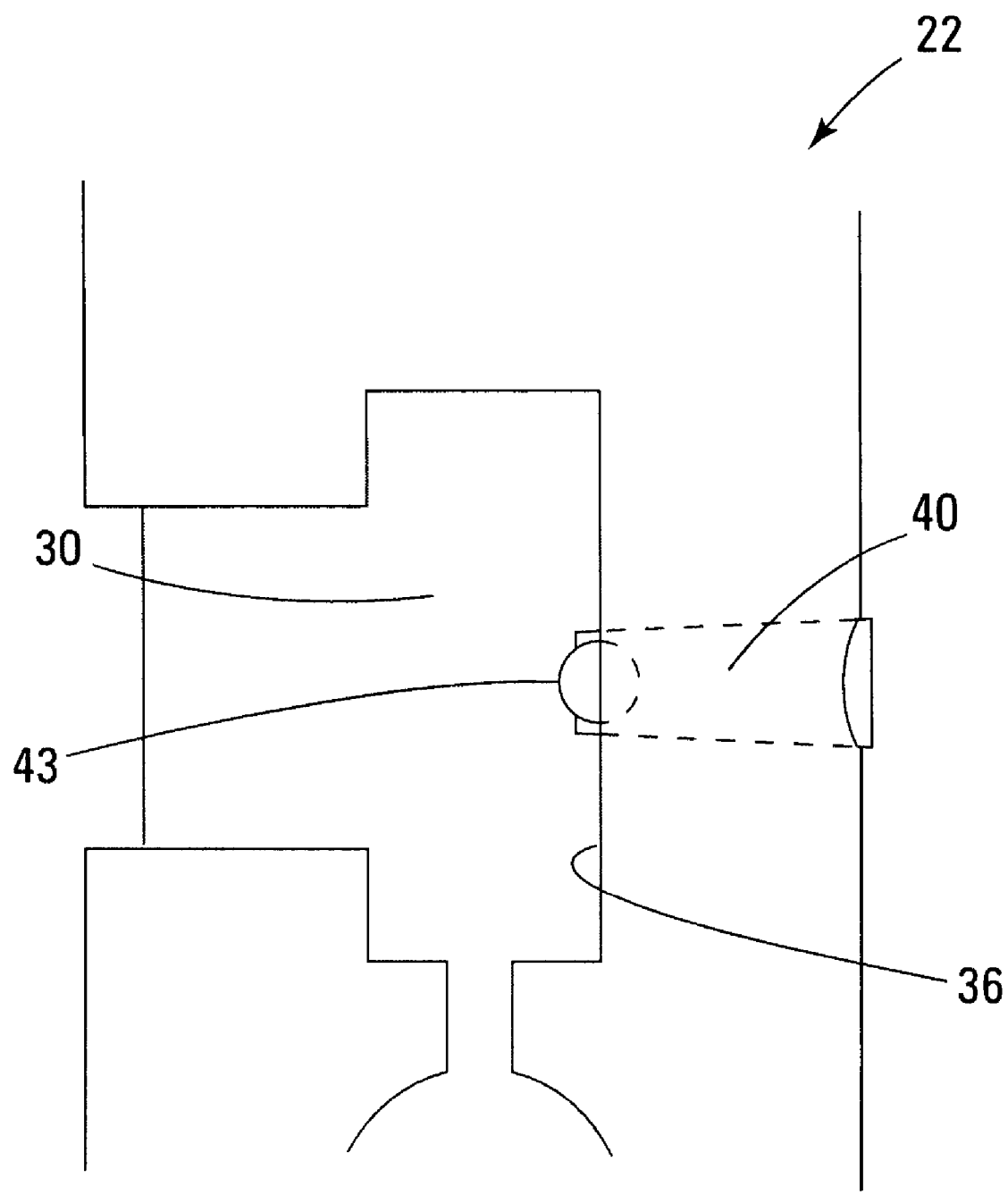
FIG. 3 is an overhead view of a seed magazine slot in the chuck.
Figure 4:
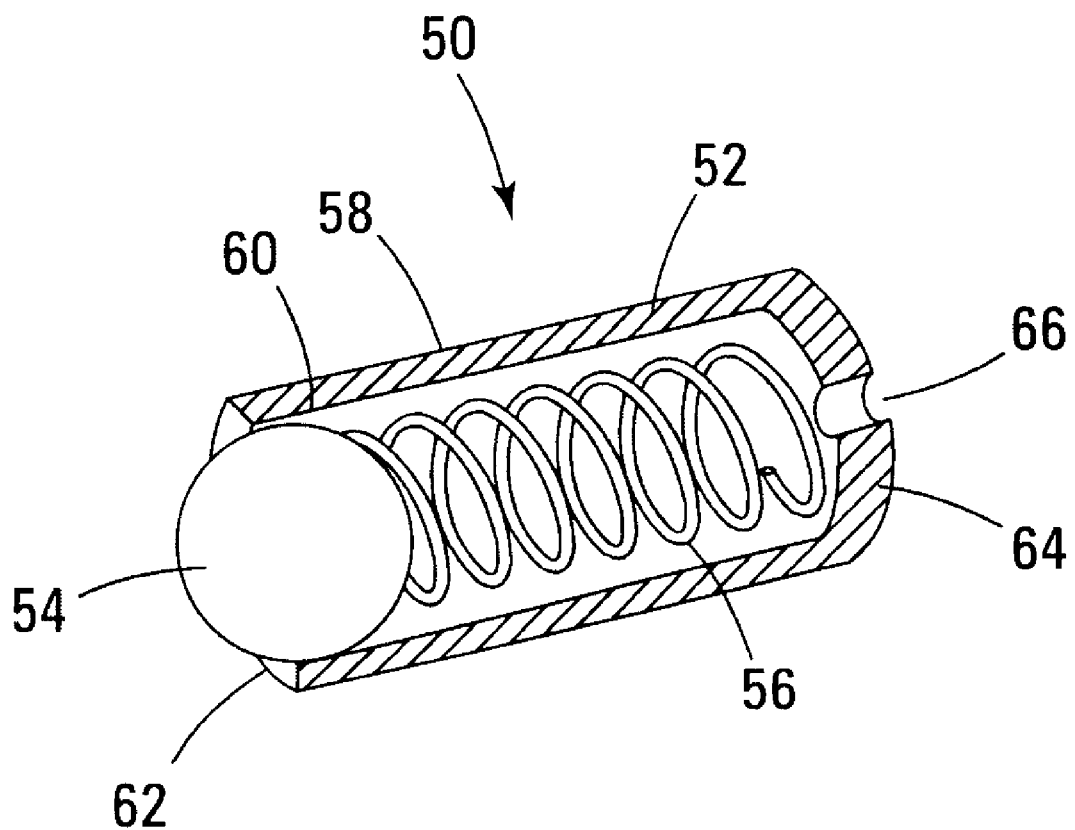
FIG. 4 is a cross-sectional side view of a ball-plunger with a vent at the end opposite the ball, showing the ball partially protruding from the shell.

With reference to FIG. 3, magazine retaining structure 40 in chuck 22 can include ball 43 such as that found in a ball-plunger (see, e.g., FIG. 4). Ball 43 can be pushed toward back surface 36 of slot 30 by a spring in the ball-plunger, and thus can protrude from back surface 36 into slot 30. When a seed magazine is being inserted into slot 30, the magazine can exert force on ball 43 and push ball 43 into the interior of magazine retaining structure 40 until a recess on the surface of the seed magazine reaches the level of ball 43. At this point, the spring in magazine retaining structure 40 can push ball 43 toward back surface 36 of slot 30, such that ball 43 protrudes from magazine retaining structure 40 and engages the recess in the magazine. The seed magazine thus will be retained in slot 30.

Figure 5:
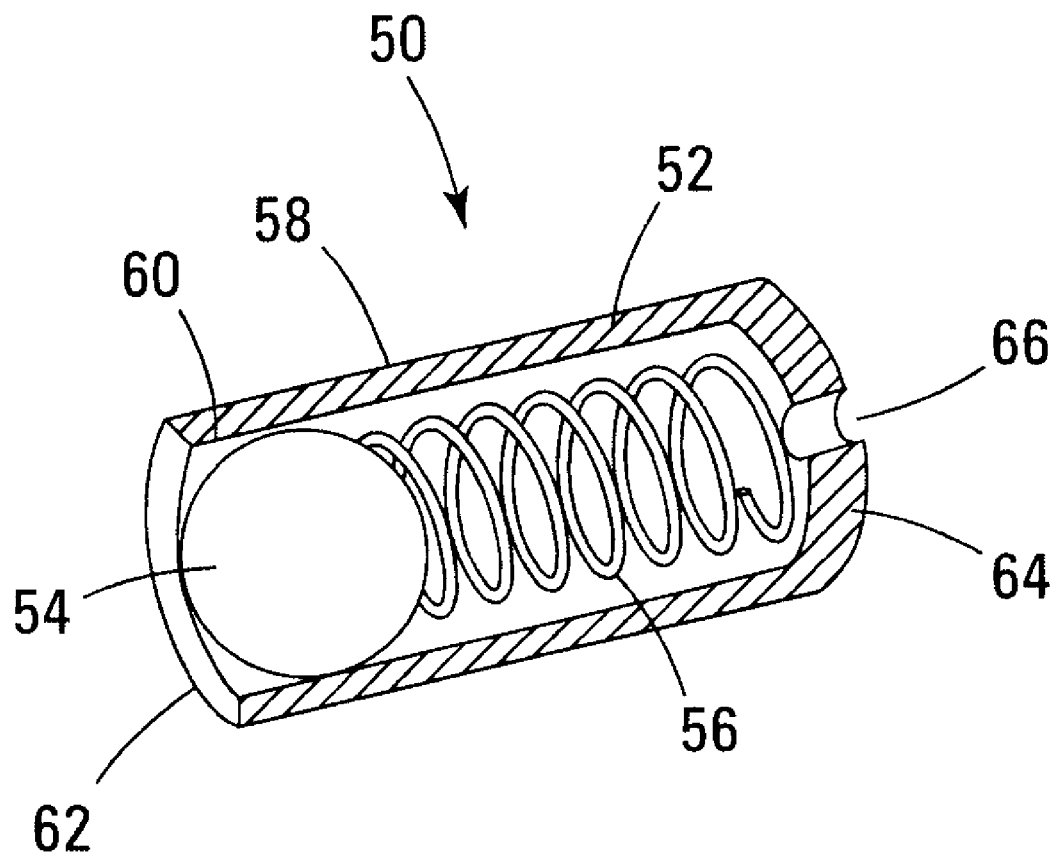
FIG. 5 is a cross-sectional side view of a ball-plunger with a vent at the end opposite the ball, showing the ball fully within the shell.

With reference to FIGS. 4 and 5, a magazine retaining structure can be ball-plunger 50. Ball-plunger 50 can have hollow shell 52, ball 54, and spring 56. Hollow shell 52 can define outer surface 58, inner surface 60, and open end 62 through which ball 54 can protrude due to force exerted upon it by spring 56. When a seed magazine is inserted into the brachytherapy applicator provided herein, the magazine can push ball 54 against spring 56 and into the interior of shell 52, as depicted in FIG. 5. FIG. 4 depicts ball-plunger 50 with ball 54 protruding from open end 62, as it would appear when engaging a seed magazine or when the seed magazine slot is empty. Shell 52 also can have distal end 64, which defines vent 66. Vent 66 can permit blood cells and other contaminating particles to exit the ball-plunger during, for example, a brachytherapy procedure or during washing or autoclaving between procedures.

Ball 54 can have any suitable shape. Ball 54 can be, for example, spherical as depicted in FIG. 4. In other embodiments, a ball can be elliptical, cubical, or block-shaped. In addition, shell 52 can have any suitable shape. For example, shell 52 can be cylindrical as depicted in FIG. 4. Alternatively, outer surface 58 of shell 52 can define another shape (e.g., a rectangular block or a triangle).

Ball 54 can be of any suitable size (e.g., more than ¼ inch, ¼ inch, ⅛ inch, ¹⁄₁₆ inch, ¹⁄₃₂ inch or less than ¹⁄₃₂ inch in diameter), provided that ball 54 is of an appropriate size to engage a seed magazine. A ball that is ¹⁄₁₆ inch in diameter is particularly useful. Inner surface 60 of shell 52 can define a hollow cavity with any diameter that is useful for movably retaining ball 54. For example, if ball 54 is 1/16 inch in diameter, inner surface 60 can define a hollow cavity that is slightly greater than 1/16 inch (e.g., 1/8 inch or 5/32 inch) in diameter. Ball 54 can protrude through open end 62 to any suitable distance, typically to a distance that allows ball 54 to engage a recess in a seed magazine. Ball 54 typically protrudes through opening 62 to a distance that is slightly less (e.g., about 15% less, about 10% less, or about 5% less) than the diameter of ball 54. A suitable distance can be, for example, 0.01 inch, 0.02 inch, 0.03 inch, 0.05 inch, 0.1 inch, 0.5 inch, or more than 0.5 inch. If ball 54 has a diameter of 1/16 inch, for example, ball 54 can protrude from open end 62 to distance that is slightly less than 1/32 inch (e.g., 0.025 inch or 0.028 inch).

Figure 6:
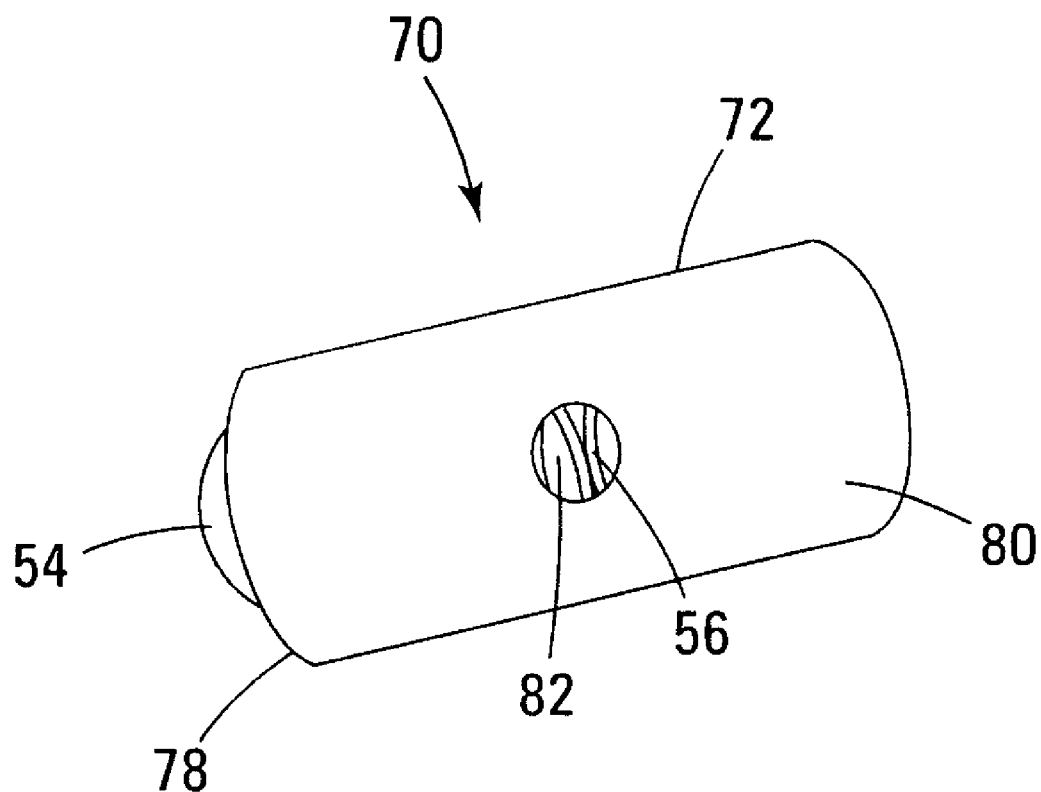
FIG. 6 is a side view of a ball-plunger with a side vent.
Figure 7:
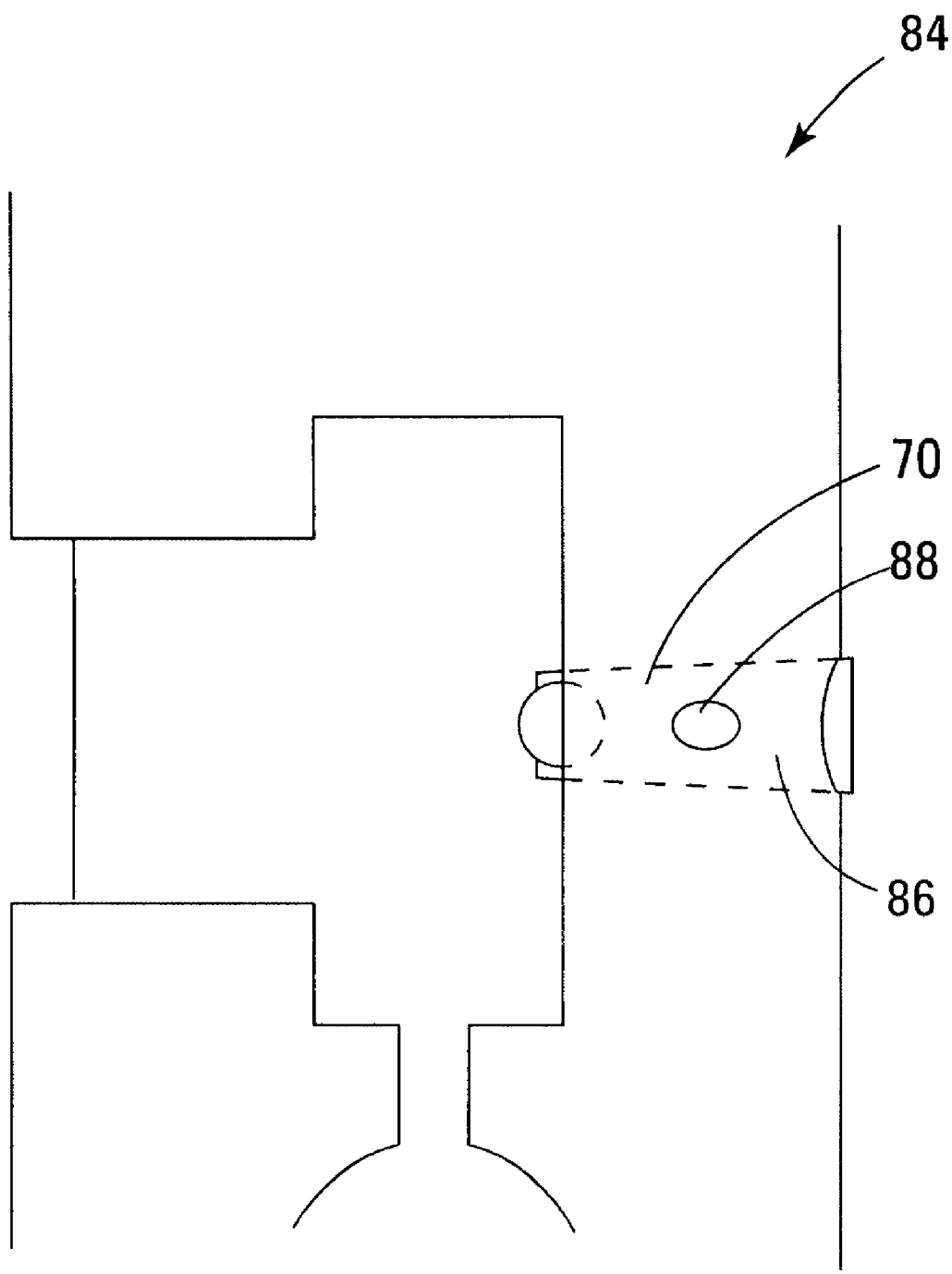
FIG. 7 is an overhead view of a chuck having a vent that lines up with a side vent in a ball-plunger.

FIG. 6 depicts a side view of ball-plunger 70, which can have hollow shell 72, ball 54, and spring 56. Hollow shell 72 can have open end 78, outer surface 80, and side vent 82 extending from outer surface 80 to the interior of hollow shell 72. Side vent 82 can permit blood cells and other contaminating particles to exit the ball-plunger. It is noted that for side vent 82 to vent to the outside of a brachytherapy apparatus, the chuck into which ball-plunger 70 is inserted also can define a vent. FIG. 7 is an overhead view of chuck 84, into which ball-plunger 70 is inserted. Chuck 84 can define outer surface 86, through which vent 88 extends toward ball-plunger 70. Ball-plunger 70 can be installed in chuck 84 such that side vent 82 lines up with vent 88, thus allowing blood cells and other contaminating particles to exit the brachytherapy applicator without becoming lodged within the ball-plunger. Hollow shell 72 can define a cavity with any diameter that is useful for movably retaining ball 54. For example, if ball 54 is 1/32 inch in diameter, the hollow cavity of shell 72 can be slightly greater than 1/32 inch (e.g., 1/16 inch or 3/64 inch) in diameter. Furthermore, ball 54 can protrude out of shell 72 to any suitable distance, typically to a distance that allows ball 54 to engage a recess in a seed magazine. A suitable distance can be, for example, 0.01 inch, 0.02 inch, 0.03 inch, 0.05 inch, 0.1 inch, 0.5 inch, or more than 0.5 inches.

Figure 8:
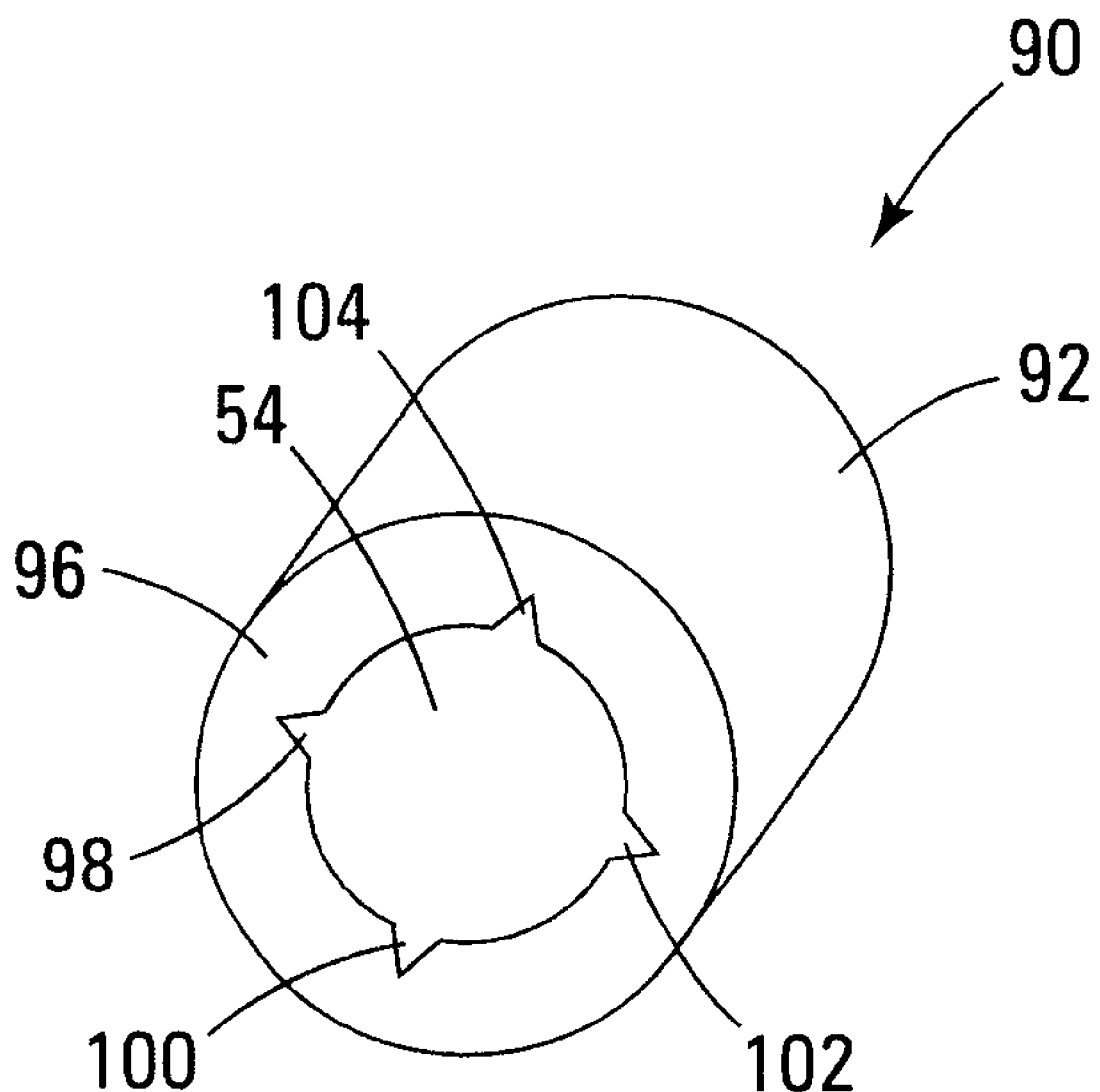
FIG. 8 is an end view of a ball-plunger with notch vents at the same end as the ball.

FIG. 8 is a front view of ball-plunger 90, which can have hollow shell 92, ball 54, and a spring. Hollow shell 92 can have open end 96, through which ball 54 can protrude due to force exerted upon it by the spring. As shown in FIG. 8, shell 92 also can have at least one notch (e.g., notches 98, 100, 102, and 104) in open end 96. Notches 98, 100, 102, and 104 are designed to permit blood cells and other contaminating particles to exit ball-plunger 90 during, for example, a brachytherapy procedure or during washing or autoclaving between procedures. The notch or notches in ball-plunger 90 can be designed such that when ball 54 is maximally pushed forward by the spring into open end 96 of hollow shell 92, at least one opening exists in hollow shell 92. In addition, hollow shell 92 can define a cavity with any diameter that is useful for movably retaining ball 54. For example, if ball 54 is 1/32 inch in diameter, the hollow cavity of shell 92 can be slightly greater than 1/32 inch (e.g., 1/16 inch or 3/64 inch) in diameter. Furthermore, ball 54 can protrude out of shell 92 to any suitable distance, typically to a distance that allows ball 54 to engage a recess in a seed magazine. A suitable distance can be, for example, 0.01 inch, 0.02 inch, 0.03 inch, 0.05 inch, 0.1 inch, 0.5 inch, or more than 0.5 inches.

Figure 9:
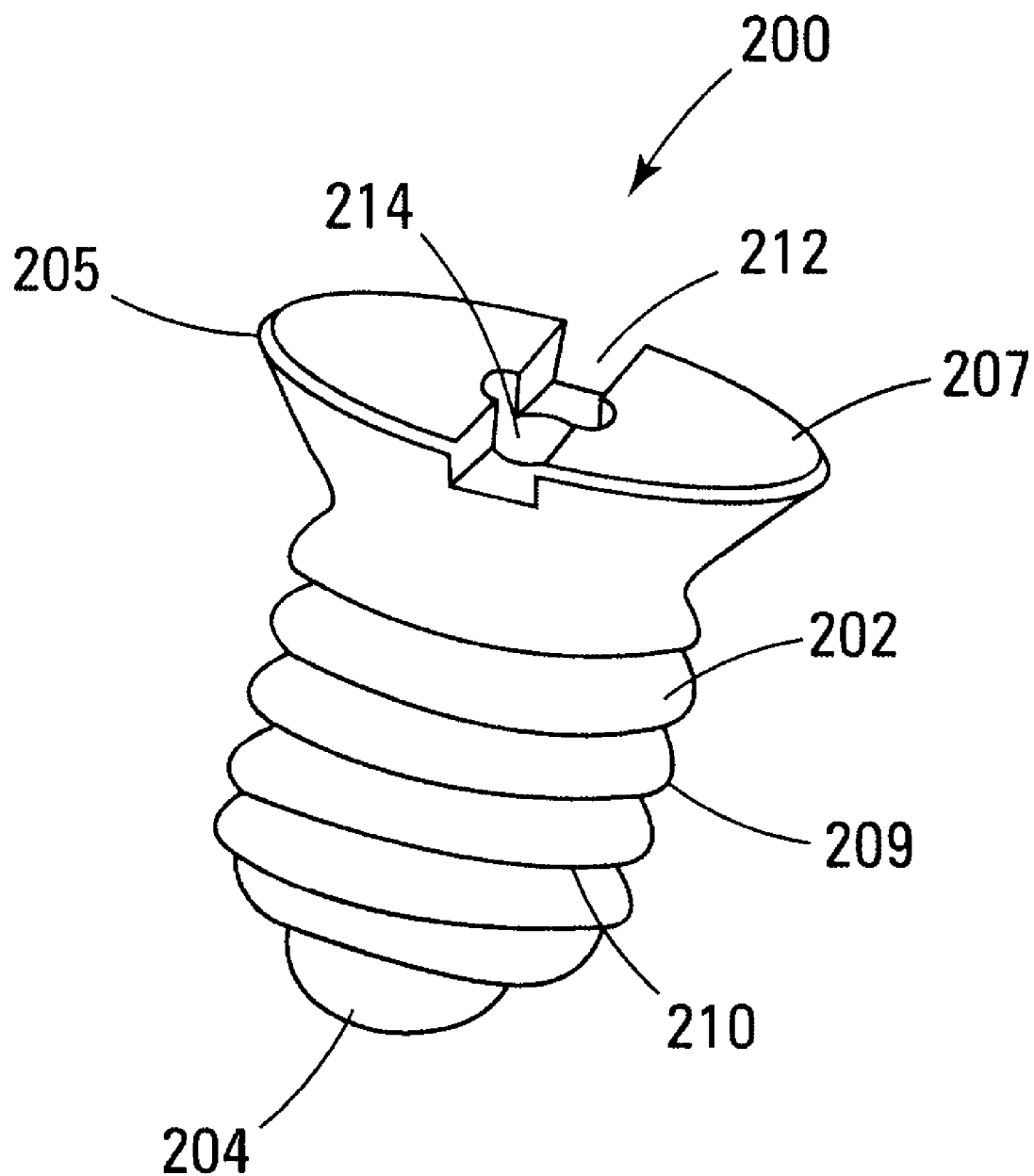
FIG. 9 is a side view of an externally threaded ball-plunger with a head.
Figure 10:
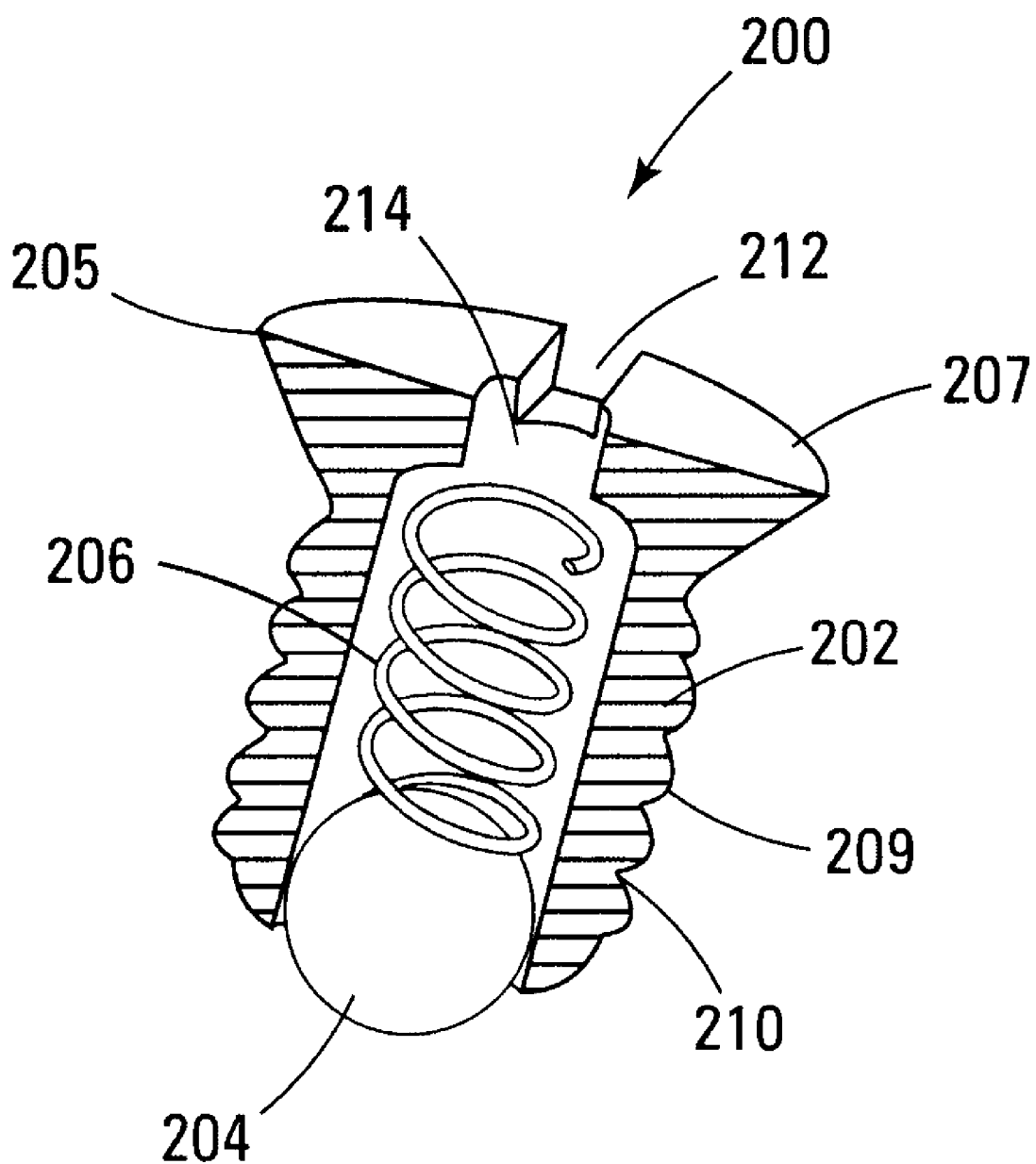
FIG. 10 is a cross-sectional view of an externally threaded ball-plunger with a head.

With reference to FIGS. 9 and 10, a magazine retaining structure can be ball-plunger 200. Ball plunger 200 can have hollow shell 202, ball 54, spring 56 (shown in FIG. 10), and head 205, which defines top surface 207 of hollow shell 202. Hollow shell 202 can define a cavity with any diameter that is useful for movably retaining ball 54. For example, if ball 54 is 1/16 inch in diameter, the hollow cavity of shell 202 can be slightly greater than 1/16 inch (e.g., 1/8 inch or 5/32 inch) in diameter. Ball 54 can protrude out of shell 202 to any suitable distance, typically to a distance that allows ball 54 to engage a recess in a seed magazine. A suitable distance can be, for example, 0.01 inch, 0.02 inch, 0.03 inch, 0.05 inch, 0.1 inch, 0.5 inch, or more than 0.5 inches.

Hollow shell 202 can define outer surface 209. As depicted in FIGS. 9 and 10, outer surface 209 can define at least one thread (e.g., thread 210). Thread 210 can be used to engage an internal thread in a brachytherapy device. Head 205 can have a recess (e.g., groove 212) configured to engage the mating end of an installation device (e.g., a flathead screwdriver, a Phillips screwdriver, or an Allen wrench) during installation or removal of ball-plunger 200 into or from a brachytherapy applicator. Head 205 also can define vent 214, which can permit blood cells and other contaminating particles to exit ball-plunger 200. A ball-plunger such as ball-plunger 200 is particularly useful because it can be readily removed from a brachytherapy applicator for cleaning. In some embodiments, ball-plunger 200 can lack vent 214. In such cases, the ball-plunger can be removed and replaced with a different ball-plunger when, for example, it becomes contaminated.

Ball-plunger 200 can be configured to resemble a hollow screw containing a ball and a spring, with a vent through the screw head. In addition, ball-plunger 200 can be configured for disassembly such that ball 54 and spring 56 can be removed from hollow shell 202 for cleaning. For example, head 205 can be configured to pull away from or screw out of shell 202, permitting removal of ball 54 and spring 56.

Figure 11:
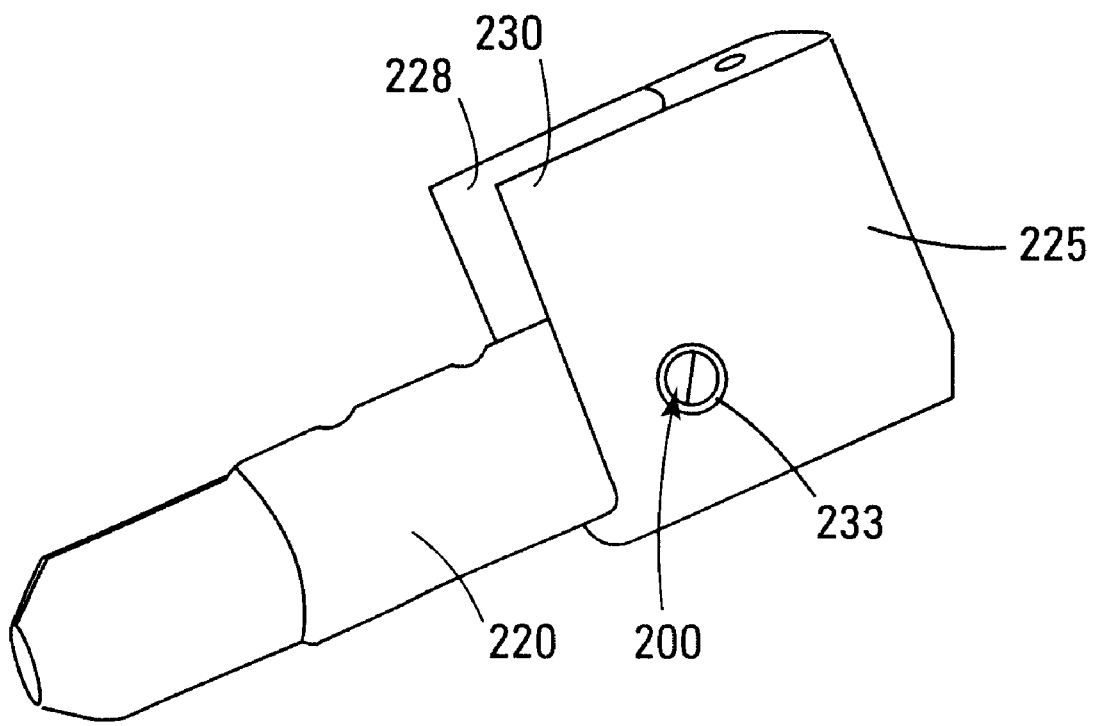
FIG. 11 is a side view of a cylindrical chuck coupled to a rectangular chuck, showing an opening through the rectangular chuck.
Figure 12:
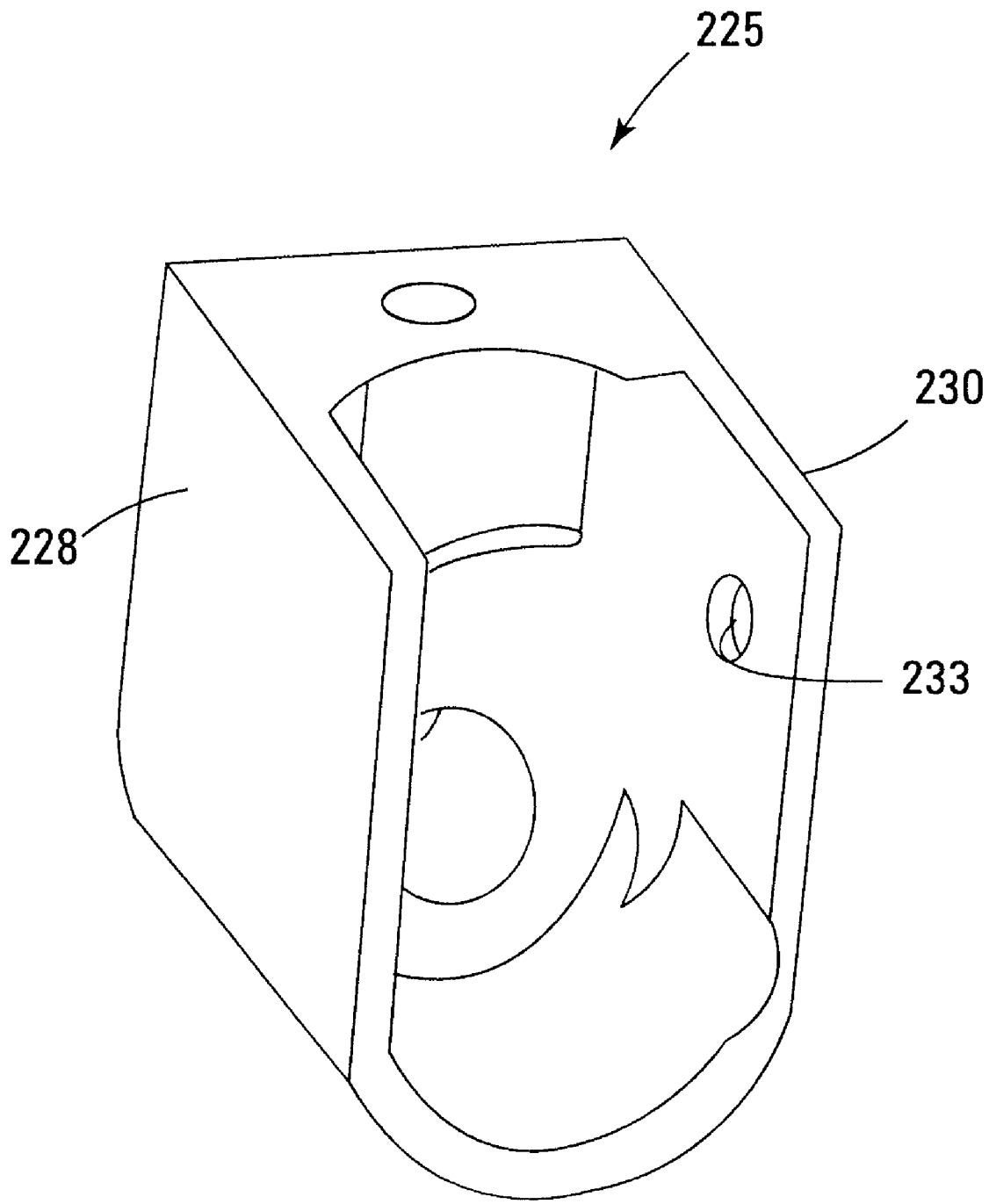
FIG. 12 is a side view of a rectangular chuck with a side opening.

A brachytherapy applicator can have both a cylindrical chuck and a rectangular chuck, with a magazine retaining structure positioned in the cylindrical chuck and the cylindrical chuck positioned in the rectangular chuck. In such an embodiment, the rectangular chuck can have an opening to permit installation and removal of a magazine retaining structure such as ball-plunger 200 (see FIGS. 9 and 10). With reference to FIG. 11, cylindrical chuck 220 can engage rectangular chuck 225. Rectangular chuck 225 can define side portion 228 and side portion 230. Side portion 230 can define opening 233, which permits access to ball-plunger 200 that is installed in cylindrical chuck 220. FIG. 12 shows a closer view of rectangular chuck 225 having side portion 228 and side portion 230, with side portion 230 defining opening 233 for access to a magazine retaining structure.

Figure 13:
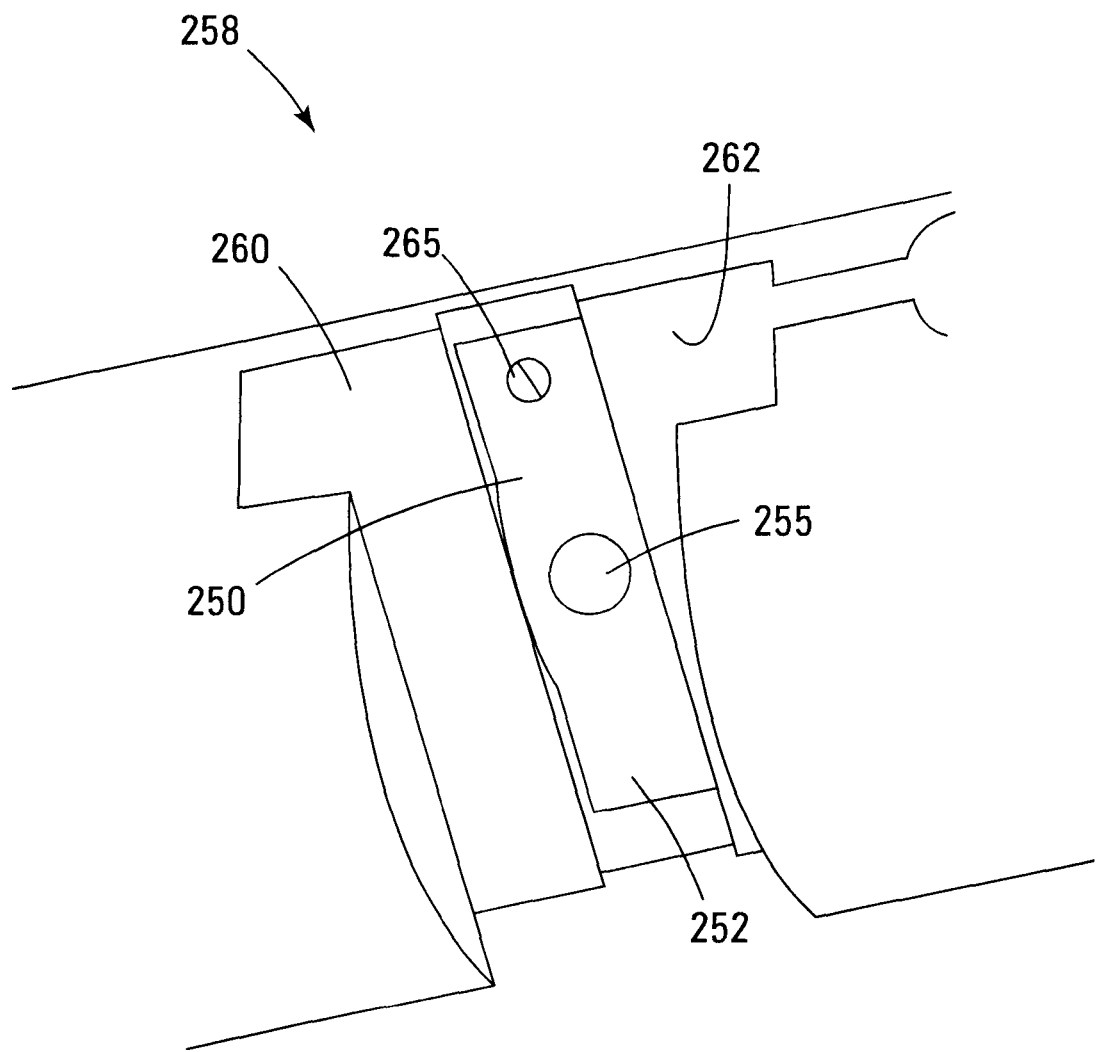
FIG. 13 is a side view of a seed magazine slot in a chuck, with a leaf spring installed in the slot as a magazine retaining structure.
Figure 14:
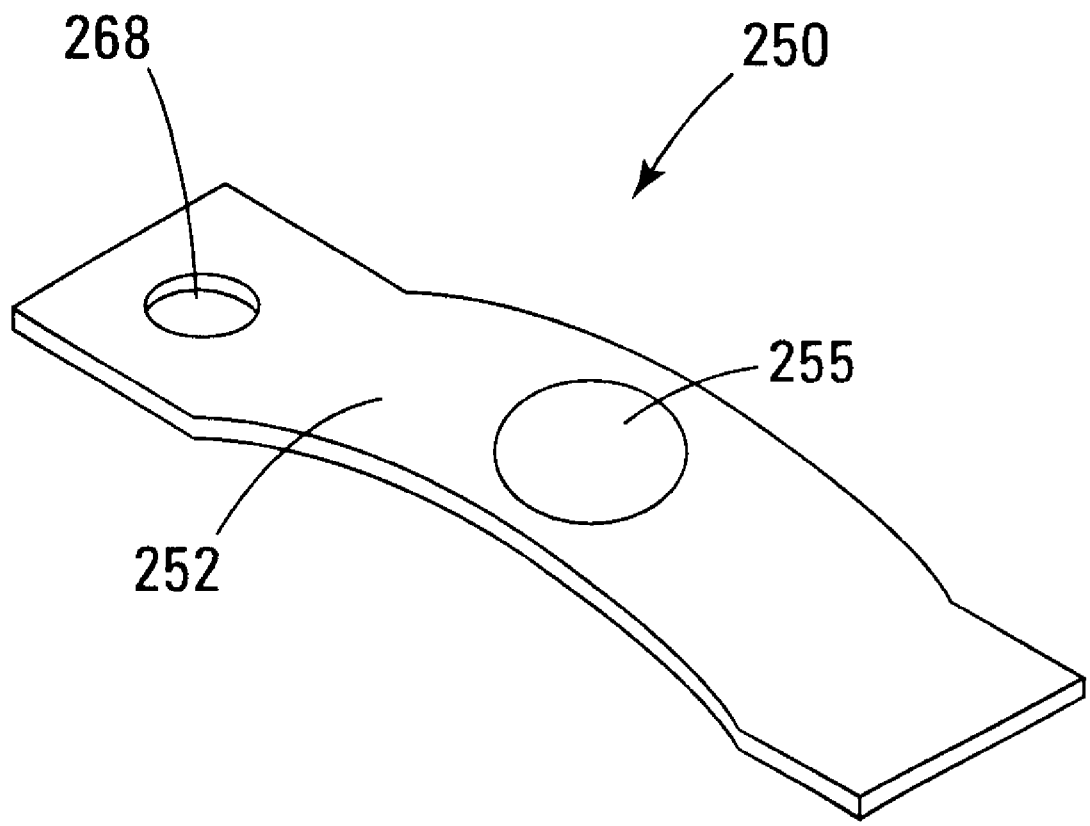
FIG. 14 is atop view of a leaf spring designed to retain a seed magazine.
Figure 15:
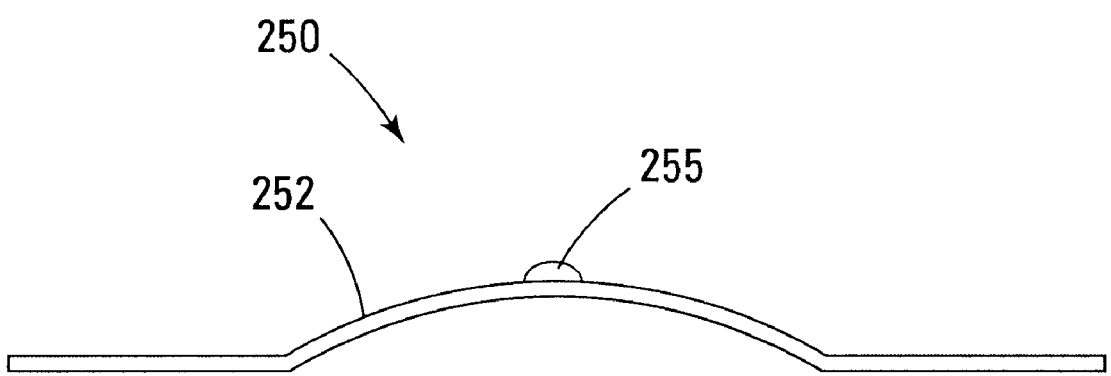
FIG. 15 is a side view of a leaf spring designed to retain a seed magazine.
Figure 16:
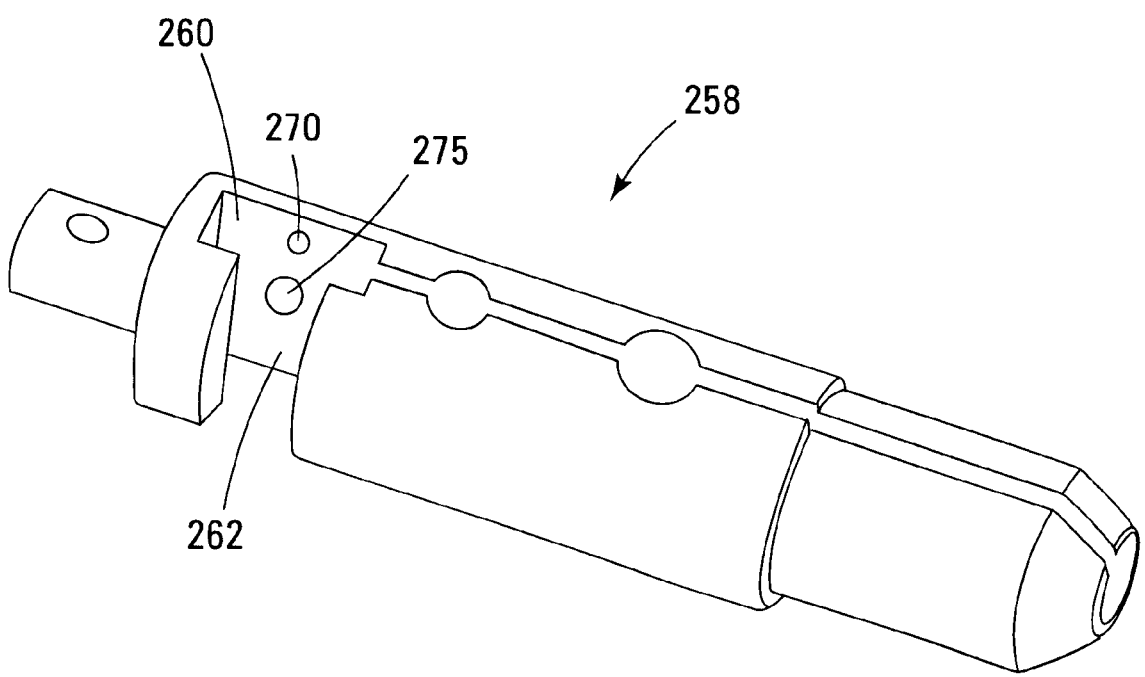
FIG. 16 is a side view of a chuck containing a vent behind the position for a magazine retaining structure.

With reference to FIGS. 13, 14, and 15, a magazine retaining device can be leaf spring 250. Leaf spring 250 can define top surface 252, which defines a protrusion (e.g., ball-like feature 255). Ball-like feature 255 can protrude from top surface 252 of leaf spring 250, and thus can engage a recess in a seed magazine. Chuck 258 can contain seed magazine slot 260, which defines back surface 262. Leaf spring 250 can be positioned on back surface 262 of slot 260, and can be attached to chuck 258 by any suitable means (e.g., screw, rivet, spot weld, press fit, or crimping). Screw 265, for example, can be installed through screw opening 268 in leaf spring 250. With reference to FIG. 16, back surface 262 of seed magazine slot 260 in chuck 258 can define screw hole 270 for installation of a leaf spring. Back surface 262 also can define vent 275, which is positioned behind the installation site for a leaf spring such as leaf spring 250. Vent 275 can permit blood cells and other contaminating particles to exit seed magazine slot 260 (e.g., during a brachytherapy procedure or during washing or autoclaving) so that leaf spring 250 does not become jammed. It is noted that if chuck 258 contains vent 275 and chuck 258 is retained within an outer chuck (e.g., an outer rectangular chuck), the outer chuck also can define a vent so that vent 275 allows contaminating particles to exit the brachytherapy device.

Leaf spring 250 can be flexible, such that when a seed magazine is being inserted into slot 260, the magazine can exert force on leaf spring 250 and push it toward back surface 262 of slot 260 until a recess on the surface of the seed magazine reaches the level of ball-like feature 255. At this point, leaf spring 250 can release away from back surface 262 of slot 260, such that ball-like feature 255 engages the recess. The seed magazine thus will be retained in slot 260.

Leaf spring 250 can be of any suitable size, and typically is designed to have a length and width to fit in seed magazine slot 260. In addition, ball-like feature 255 can have any suitable shape (e.g., hemispherical, cubical, conical, or ovoid). Ball-like feature also can have any suitable diameter and height (i.e., the distance between top surface 252 and most distal point of ball-like feature 255), provided that leaf spring 250 can engage a seed magazine. For example, ball-like feature can have a diameter between ½ inch and 1/64 inch (e.g., ¼ inch, ⅛ inch, 1/16 inch, or 1/32 inch). In addition, ball-like feature can have a height between 0.005 inch and 0.2 inch (e.g., 0.008 inch, 0.01 inch, 0.02 inch, 0.05 inch, 0.1 inch, or 0.18 inch).

Figure 17:
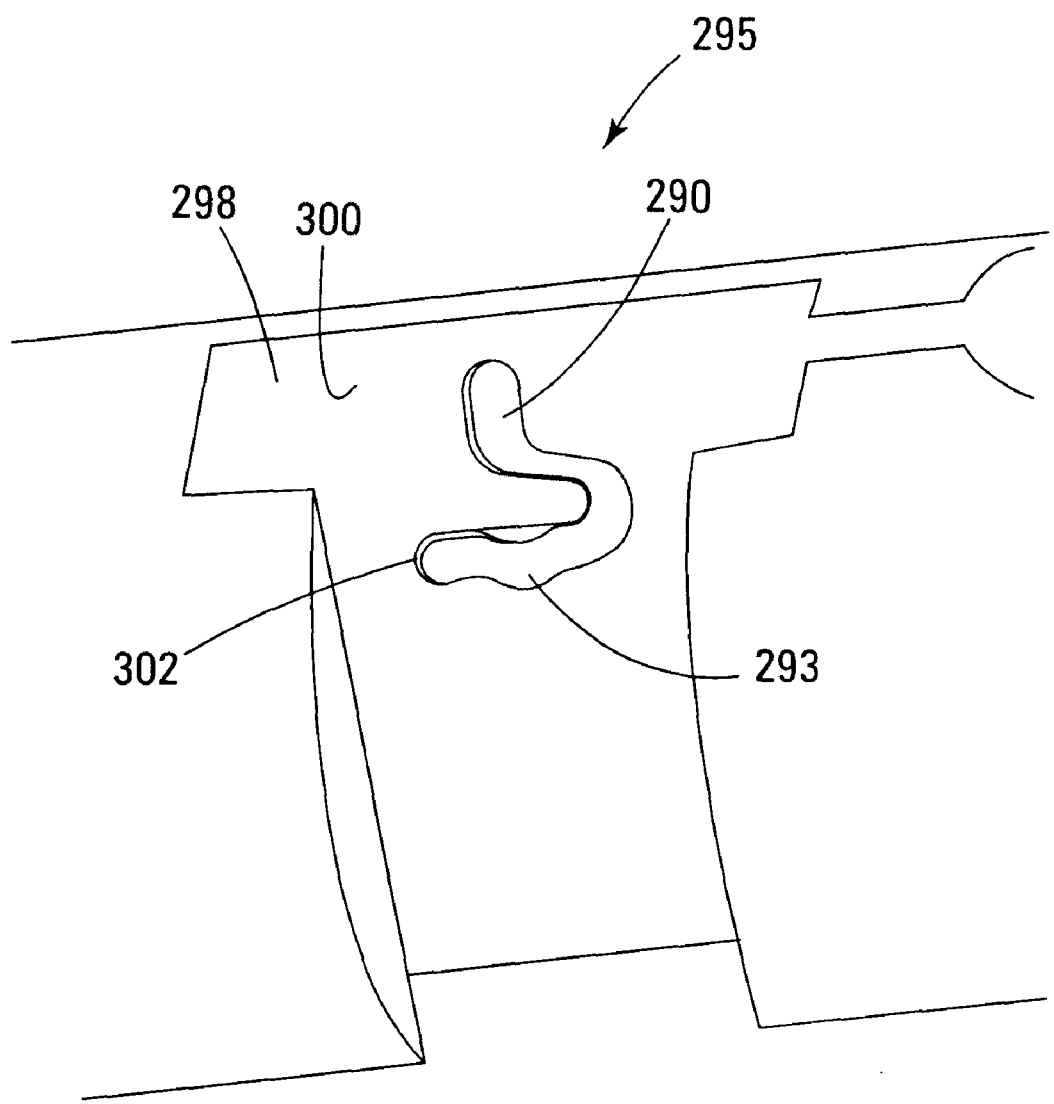
FIG. 17 is a side view of a seed magazine slot in a chuck, with a wire installed in the slot as a magazine retaining structure.
Figure 18:
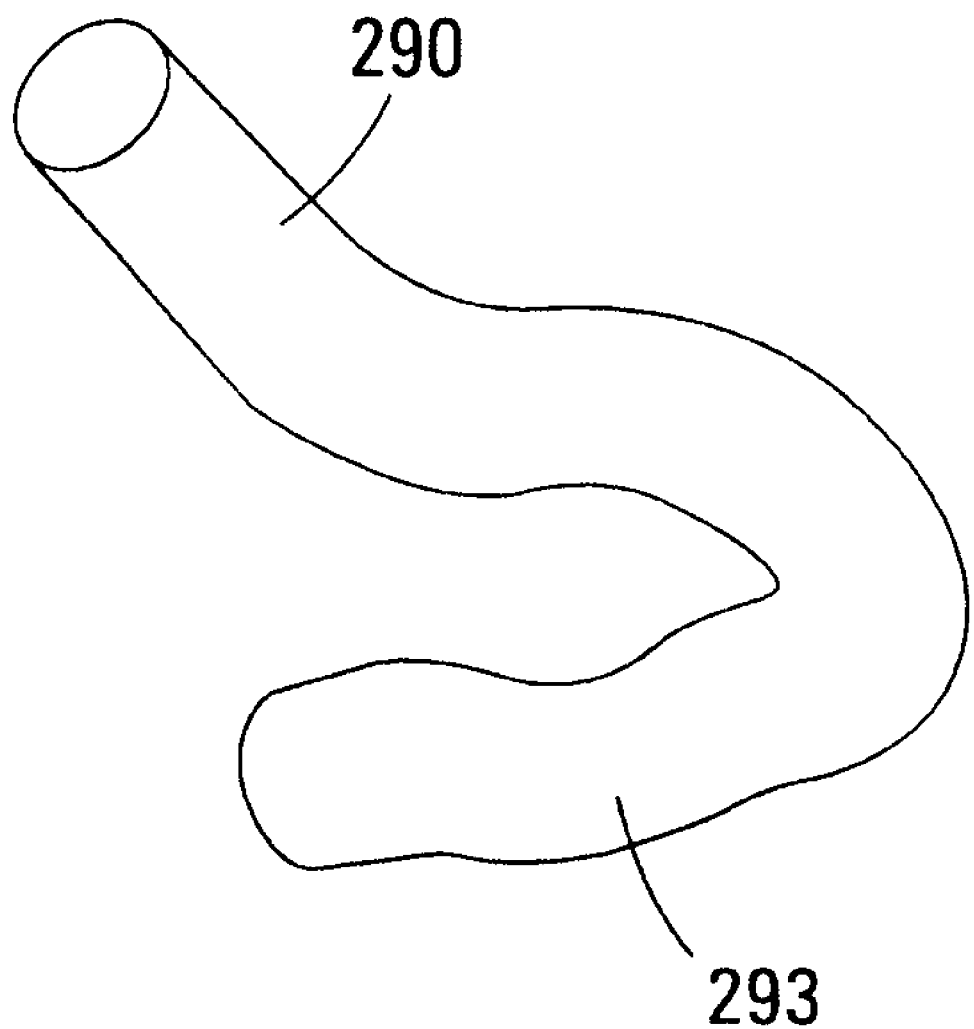
FIG. 18 is an overhead view of a wire for designed to retain a seed magazine.
Figure 19:
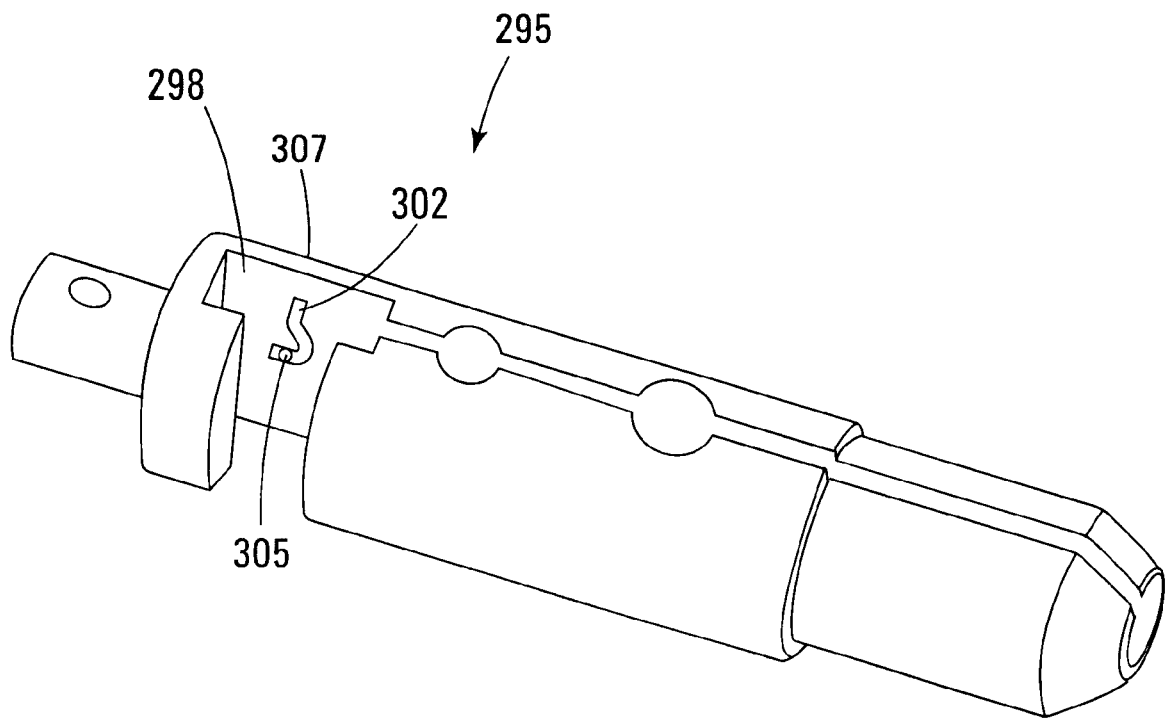
FIG. 19 is a side view of a chuck containing a groove, with a vent located in the groove behind the position for a wire magazine retaining structure.

With reference to FIGS. 17 and 18, a magazine retaining structure can be fashioned from formed wire, such as wire 290. Wire 290 can define bulge 293, which protrudes out of the plane in which the rest of wire 290 is positioned in chuck 295. Bulge 293 can engage a recess in a seed magazine and thus retain a seed magazine within a brachytherapy applicator. While wire 290 is curved as shown in FIGS. 17 and 18, a wire magazine retaining structure can have any suitable shape provided that it has a bulge for retaining a seed magazine. Wire 290 can be installed either reversibly or permanently in chuck 295, by any suitable means (e.g., press fitting, spot welding, or crimping). Chuck 295 can contain seed magazine slot 298, which defines back surface 300. Back surface 300 can define groove 302 for receiving wire 290. As shown in FIG. 17, wire 290 can be positioned in groove 302 such that only bulge 293 protrudes above back surface 300 of seed magazine slot 298. With reference to FIG. 19, groove 302 also can define vent 305 that extends from behind the position of wire 290 through chuck 295, to outer surface 307 of chuck 295. Vent 305 can allow blood cells and other contaminating particles to exit seed magazine slot 298 (e.g., during washing or autoclaving). If chuck 295 contains vent 305 and is retained within an outer chuck (e.g., an outer rectangular chuck), the outer chuck also can define a vent so that contaminating particles can exit the brachytherapy device.

Wire 290 can be flexible, such that when a seed magazine is being inserted into slot 298, the magazine can exert force on wire 290 and push it toward back surface 300 of slot 298 until a recess on the surface of the seed magazine reaches the level of bulge 293. At this point, wire 290 can flex away from back surface 300 of slot 298, such that bulge 293 engages the recess. The seed magazine thus will be retained in slot 298.

As noted above, wire 290 can have any suitable shape. Furthermore, the distance between the plane in which most of wire 290 lies and the most distal point of bulge 293 can be any distance suitable for wire 290 to engage a seed magazine. The distance typically is between 0.005 inch and 0.2 inch (e.g., 0.007 inch, 0.01 inch, 0.02 inch, 0.05 inch, 0.1 inch, or 0.18 inch).

Figure 20:
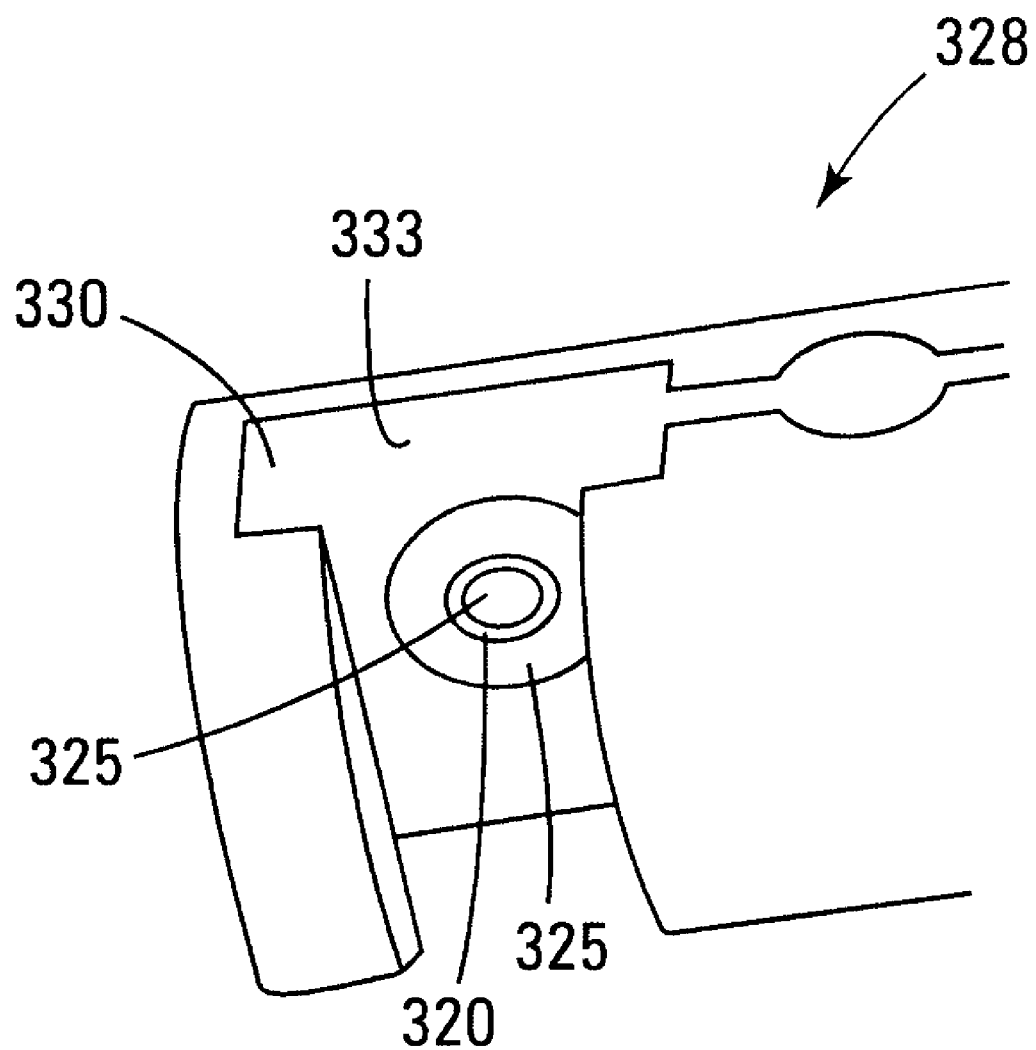
FIG. 20 is a side view of a seed magazine slot in a chuck, with a modified Bellville spring installed in the slot as a magazine retaining structure.
Figure 21:
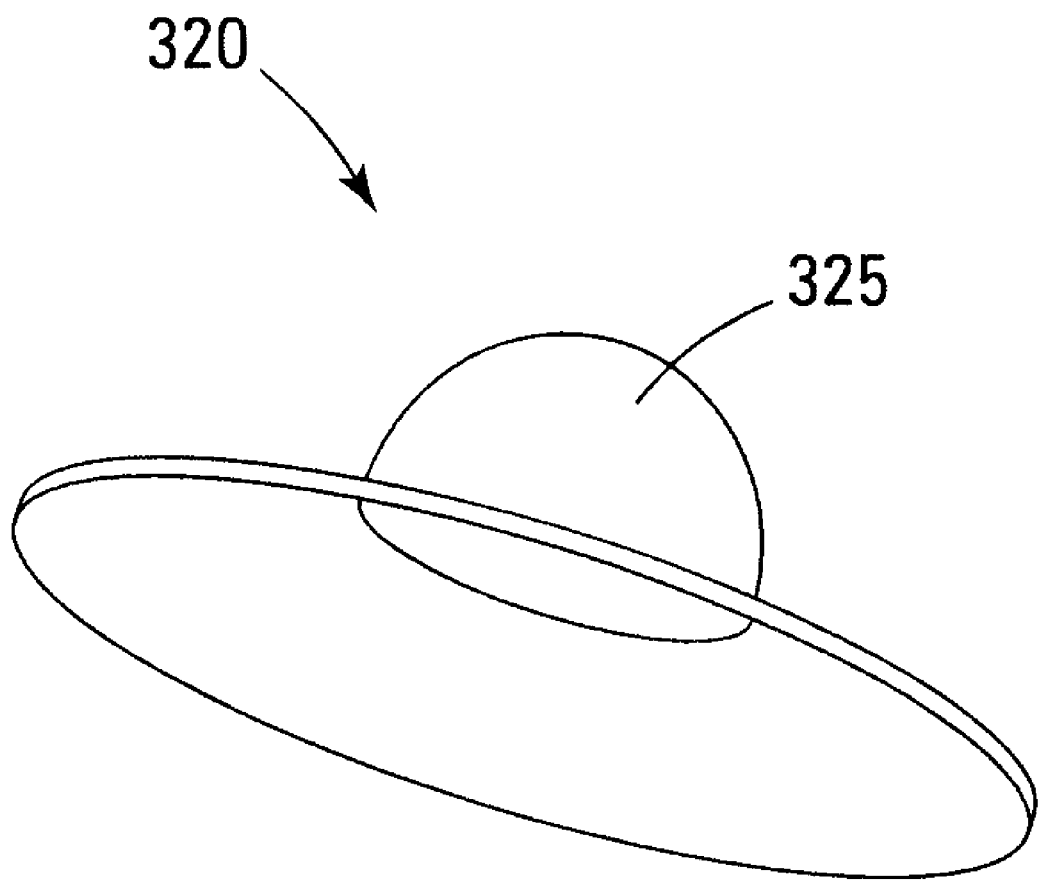
FIG. 21 is a side view of a modified Bellville spring designed to retain a seed magazine.

With reference to FIGS. 20 and 21, a magazine retaining device can be a Bellville spring such as modified Bellville spring 320. Modified Bellville spring 320 can define a protrusion (e.g., central dome 325), which protrudes from the spring and can engage a recess in a seed magazine in order to retain a seed magazine in a brachytherapy applicator. Chuck 328 can define seed magazine slot 330, which defines back surface 333. Modified Bellville spring 320 can be installed on back surface 333 such that central dome 325 protrudes into slot 330 and thus can engage a seed magazine inserted into slot 330. Modified Bellville spring 320 can be installed in chuck 328 by any suitable means (e.g., screw, rivet, press fit, spot weld, or crimping). Back surface 333 can define recess 335 into which modified Bellville spring 320 can be installed (e.g., reversibly or permanently), such that only central dome 325 protrudes from back surface 333. Alternatively, modified Bellville spring 320 can be reversibly or permanently installed on back surface 333. Recess 335 or back surface 333 also can define a vent (see, e.g., vent 275 in FIG. 16) such that blood cells and other contaminating particles can be removed from the vicinity of the seed magazine retaining structure during, for example, washing or autoclaving. Again, if chuck 328 is seated in an outer chuck (e.g., an outer rectangular chuck), the outer chuck also can define a vent such that contaminating particles can exit the brachytherapy device.

Modified Bellville spring 320 can be flexible, such that when a seed magazine is being inserted into slot 330, the magazine can exert force on modified Bellville spring 320 and push it toward back surface 333 of slot 330 until a recess on the surface of the seed magazine reaches the level of central dome 325. At this point, modified Bellville spring 320 can release and away from back surface 333 of slot 330, such that central dome 325 engages the recess. The seed magazine thus will be retained in slot 330.

Central dome 325 can have any suitable shape (e.g., hemispherical, cubic, conical, or ovoid), provided that modified Bellville spring can engage a seed magazine. Modified Bellville spring 320, and particularly central dome 325 of spring 320, also can have any suitable diameter and height. A central dome can have a diameter between ½ inch and 1/64 inch (e.g., ¼ inch, ⅛ inch, 1/16 inch, or 1/32 inch). In addition, central dome 325 can have a height between 0.2 inch and 0.005 inch (e.g., 0.1 inch, 0.1 inch, 0.05 inch, 0.02 inch, or 0.01 inch).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A brachytherapy applicator comprising a needle and a chuck, wherein said chuck comprises a slot for receiving a magazine containing radioactive seeds, wherein said chuck is positioned such that said seeds are delivered from said magazine to said needle, wherein said chuck further comprises a magazine retaining structure, and wherein said magazine retaining structure comprises a leaf spring comprising at least one protrusion.

2. The brachytherapy applicator of claim 1, wherein said leaf spring comprises a ball like feature.

3. The brachytherapy applicator of claim 1, wherein said chuck defines a vent, and wherein said vent is positioned behind said leaf spring.

4. A brachytherapy applicator comprising a needle and a chuck, wherein said chuck comprises a slot for receiving a magazine containing radioactive seeds, wherein said chuck is positioned such that said seeds are delivered from said magazine to said needle, wherein said chuck further comprises a magazine retaining structure, and wherein said magazine retaining structure comprises a wire having a bulge.

5. The brachytherapy applicator of claim 4, wherein said chuck defines a groove, and wherein said wire is in said groove.

6. The brachytherapy applicator of claim 5, wherein said chuck defines a vent, and wherein said vent is positioned behind said bulge.

7. A brachytherapy applicator comprising a needle and a chuck, wherein said chuck comprises a slot for receiving a magazine containing radioactive seeds, wherein said chuck is positioned such that said seeds are delivered from said magazine to said needle, wherein said chuck further comprises a magazine retaining structure, and wherein said magazine retaining structure comprises a Bellville spring comprising a protrusion.

8. The brachytherapy applicator of claim 7, wherein said protrusion is a central dome.

9. The brachytherapy applicator of claim 7, wherein said chuck defines a vent, and wherein said vent is positioned behind said Bellville spring.

10. A brachytherapy applicator comprising a needle and a chuck, wherein said chuck comprises a slot for receiving a magazine containing radioactive seeds, wherein said chuck is positioned such that said seeds are delivered from said magazine to said needle, wherein said chuck further comprises a magazine retaining structure, and wherein said magazine retaining structure is a component that contains at least two openings and comprises:

(a) a hollow shell having a first end, wherein said first end defines an opening, and wherein said shell comprises a vent, said opening and said vent being said at least two openings;

(b) a ball, wherein said shell retains said ball such that said ball is movably positioned at least partially within said shell; and (c) a spring, wherein said shell retains said spring such that said spring exerts force against said ball such that said ball is pushed toward said first end to a position where said ball partially protrudes through said opening.

11. The brachytherapy applicator of claim 10, wherein said shell defines a second end, and wherein said vent is positioned at said second end.

12. The brachytherapy applicator of claim 10, wherein said shell defines a side region, and wherein said vent is positioned in said side region.

13. The brachytherapy applicator of claim 10, wherein said vent is accessible through said chuck.

14. The brachytherapy applicator of claim 10, wherein at least a portion of an outer surface of said shell contains a thread.

15. The brachytherapy applicator of claim 14, wherein said chuck defines first and second side portions, and wherein at least one of said side portions comprises an opening capable of receiving said magazine retaining structure.

16. A brachytherapy applicator comprising a needle and a chuck, wherein said chuck comprises a slot for receiving a magazine containing radioactive seeds, wherein said chuck is positioned such that said seeds are delivered from said magazine to said needle, wherein said chuck further comprises a magazine retaining structure selected from the group consisting of a solid component and a component that contains at least two openings and wherein said magazine retaining structure is removable from said applicator.

17. The brachytherapy applicator of claims 1, 4, 7, or 10, wherein said magazine retaining structure is plastic, bronze, or stainless steel.

18. A brachytherapy applicator comprising a needle and a chuck, wherein said chuck comprises:

(a) a slot for receiving a magazine containing radioactive seeds, wherein said chuck is positioned such that said seeds are delivered from said magazine to said needle; and (b) a magazine retaining structure, said magazine retaining structure comprising:

(i) a hollow shell, wherein said hollow shell defines a first end and a second end, wherein said first end defines an opening;

(ii) a ball, wherein said ball is movably positioned at least partially within said hollow shell; and (iii) a spring, wherein said spring exerts force against said ball in a direction toward said first end such that said ball partially protrudes through said opening, and wherein at least one open space exists when said ball is fully engaged within said opening.

19. The brachytherapy applicator of claim 18, wherein said hollow shell defines a vent.

20. The brachytherapy applicator of claim 19, wherein said vent is at said second end.

21. The brachytherapy applicator of claim 19, wherein said shell defines a side region, and wherein said side region defines said vent.

* * * * *

UNITED STATES PATENT AND TRADEMARK OFFICE
CERTIFICATE OF CORRECTION

PATENT NO.     : 6,656,107 B1
DATED          : December 2, 2003
INVENTOR(S)    : Laust Pedersen and Jerry Barber It is certified that error appears in the above-identified patent and that said Letters Patent is hereby corrected as shown below:

Title page,
Item [56], References Cited, U.S. PATENT DOCUMENTS, please insert
-- 4,402,308   9/83   Scott
  4,461,280   7/84   Baumgartner
  4,700,692  10/87  Baumgartner
  5,242,373   9/93   Scott et al.
  5,860,909   1/99   Mick et al. --

Column 12,
Line 23, please insert a comma after "openings".

Signed and Sealed this

Eighteenth Day of May, 2004

JON W. DUDAS
*Acting Director of the United States Patent and Trademark Office*